United States Patent
Sasahara et al.

(10) Patent No.: US 11,633,585 B2
(45) Date of Patent: Apr. 25, 2023

(54) MEDICAL CONNECTOR

(71) Applicant: Nikkiso Company Limited, Tokyo (JP)

(72) Inventors: Shigeru Sasahara, Shizuoka (JP); Kazuhide Ono, Shizuoka (JP); Ryo Kato, Shizuoka (JP); Hironobu Sugiyama, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 835 days.

(21) Appl. No.: 16/562,245

(22) Filed: Sep. 5, 2019

(65) Prior Publication Data

US 2019/0388674 A1    Dec. 26, 2019

Related U.S. Application Data

(63) Continuation of application No. PCT/JP2018/011536, filed on Mar. 22, 2018.

(30) Foreign Application Priority Data

Mar. 22, 2017 (JP) .............................. JP2017-055794

(51) Int. Cl.
*A61M 39/20* (2006.01)
*A61M 39/10* (2006.01)
*A61M 1/36* (2006.01)

(52) U.S. Cl.
CPC .......... *A61M 39/20* (2013.01); *A61M 1/3643* (2013.01); *A61M 39/105* (2013.01); *A61M 2039/205* (2013.01)

(58) Field of Classification Search
CPC .... A61M 39/20; A61M 39/105; A61M 39/16; A61M 39/162; A61M 39/165;
(Continued)

(56) References Cited

U.S. PATENT DOCUMENTS 6,328,726 B1 * 12/2001 Ishida ................. A61M 1/0236
604/408
8,641,684 B2 * 2/2014 Utterberg .............. A61M 1/367
604/1
(Continued)

FOREIGN PATENT DOCUMENTS

| GB | 2414678 A | * | 12/2005 | ........ A61M 25/0075 |
|---|---|---|---|---|
| JP | 2009-101093 | | 5/2009 | |
| JP | 2009101093 A | * | 5/2009 | |

OTHER PUBLICATIONS

International Search Report from the Japanese Patent Office for Application No. PCT/JP2018/011536 dated Jun. 12, 2018.
(Continued)

*Primary Examiner* — Amber R Stiles
*Assistant Examiner* — Leah J Swanson
(74) *Attorney, Agent, or Firm* — Young Basile Hanlon & MacFarlane, P.C.

(57) ABSTRACT

A medical connector that allows ventilation of vapor used in vapor sterilization and has an internal flow route that is tightly closable without using any separate clamping device. A medical connector includes a body having an internal flow route connected to an other flow route, proximal portions included in the body and having respective one-side connection ports at which the internal flow route is connectable to the one flow route, a distal portion having an other-side connection port at which the internal flow route is connectable to the other flow route, one-side lid portion, and an other-side lid portion whose state is switchable between a closing state and a ventilating state in which the other-side lid portion covers the other-side connection port such that ventilation is allowed.

17 Claims, 9 Drawing Sheets

(58) Field of Classification Search
CPC .......... A61M 39/18; A61M 2039/0288; A61M 2039/0036; A61M 2039/266; A61M 2039/0285; A61M 2039/167; A61M 1/3643

See application file for complete search history.

(56) References Cited

U.S. PATENT DOCUMENTS

| | | | |
|---|---|---|---|
| 2008/0287906 A1* | 11/2008 | Burkholz | A61M 25/0693 |
| | | | 604/533 |
| 2014/0228815 A1* | 8/2014 | Haag | A61M 39/10 |
| | | | 604/535 |
| 2016/0121097 A1* | 5/2016 | Steele | F16L 55/1152 |
| | | | 29/428 |
| 2016/0143815 A1* | 5/2016 | Koelper | A61M 39/105 |
| | | | 604/533 |
| 2016/0354595 A1 | 12/2016 | Gallagher | |

OTHER PUBLICATIONS

European Search Report for Application No. 18770704.7 dated Nov. 3, 2020.

\* cited by examiner

[Fig. 1]
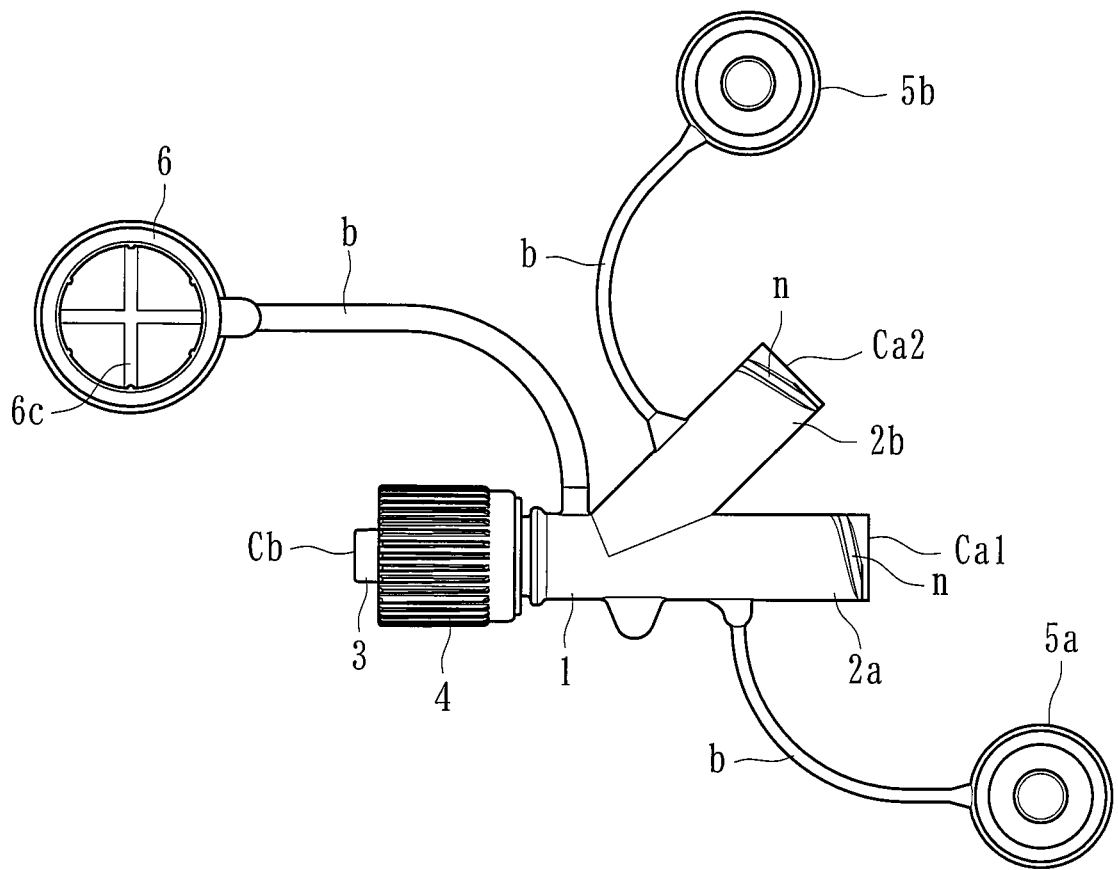
[Fig. 2]
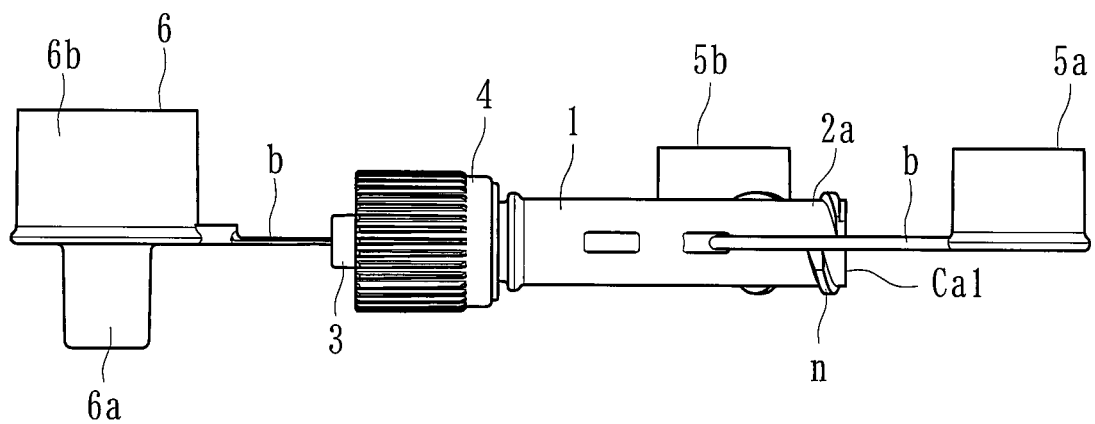

[Fig. 3]
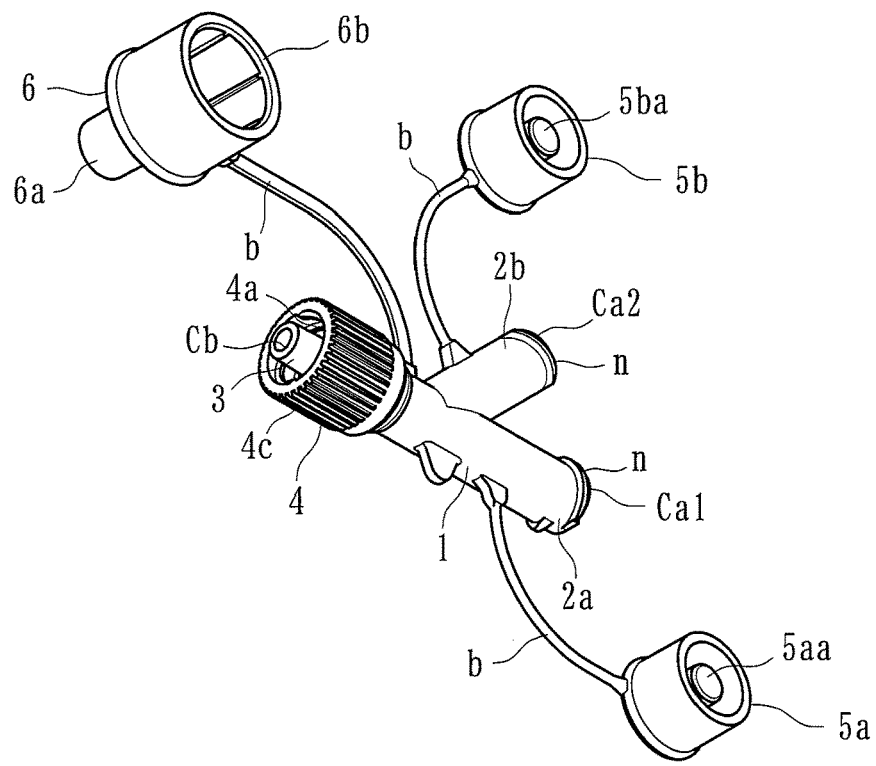
[Fig. 4]
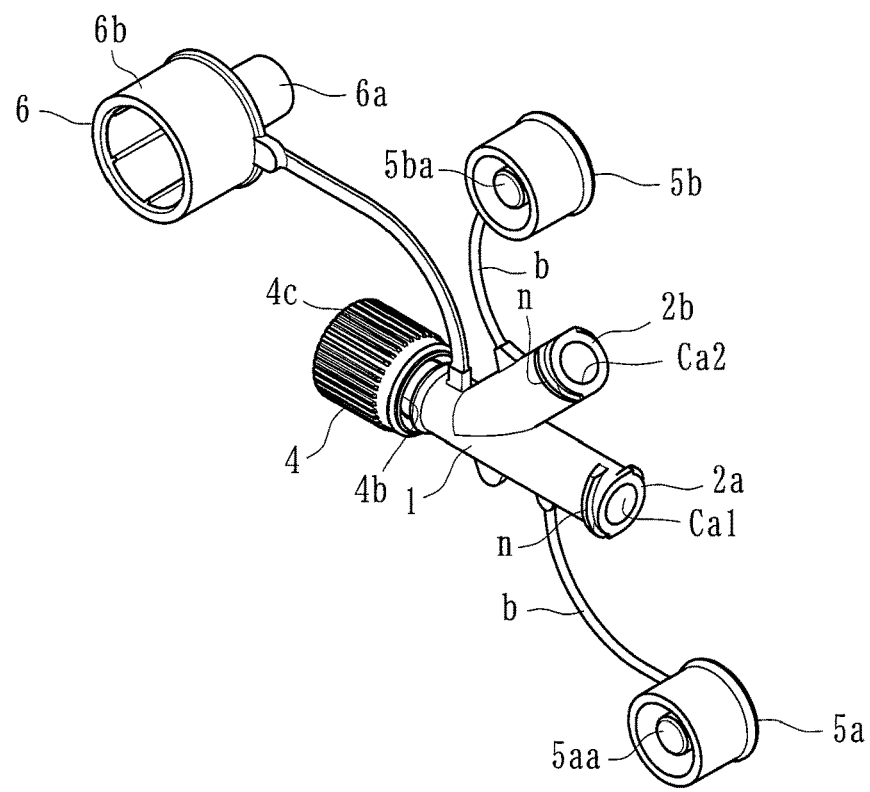

[Fig. 5]
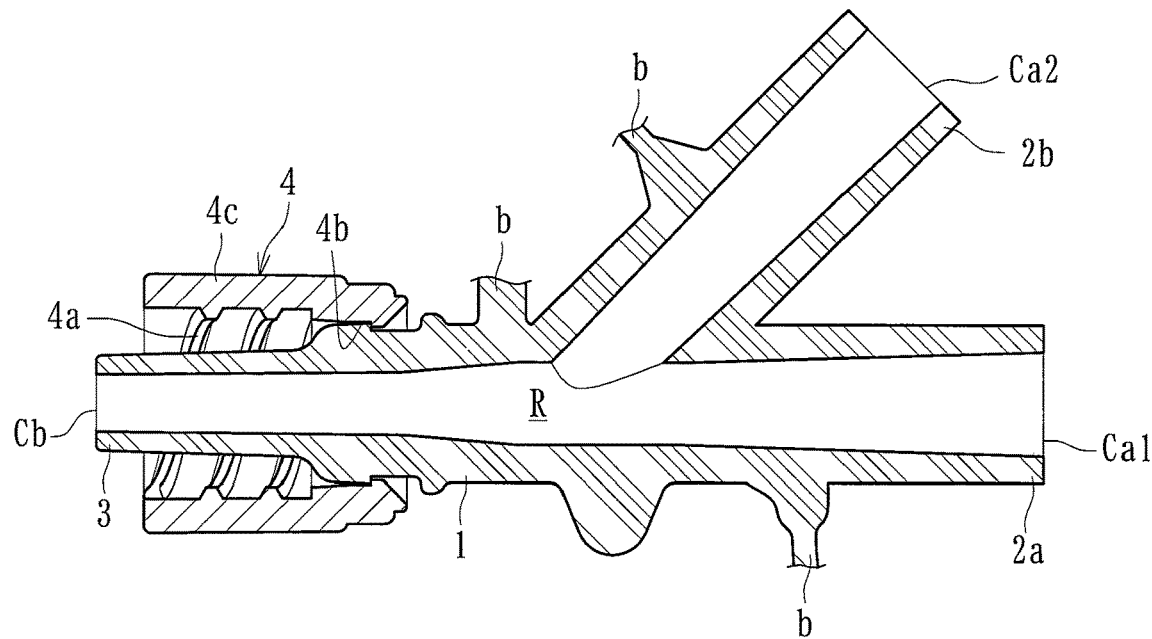
[Fig. 6]
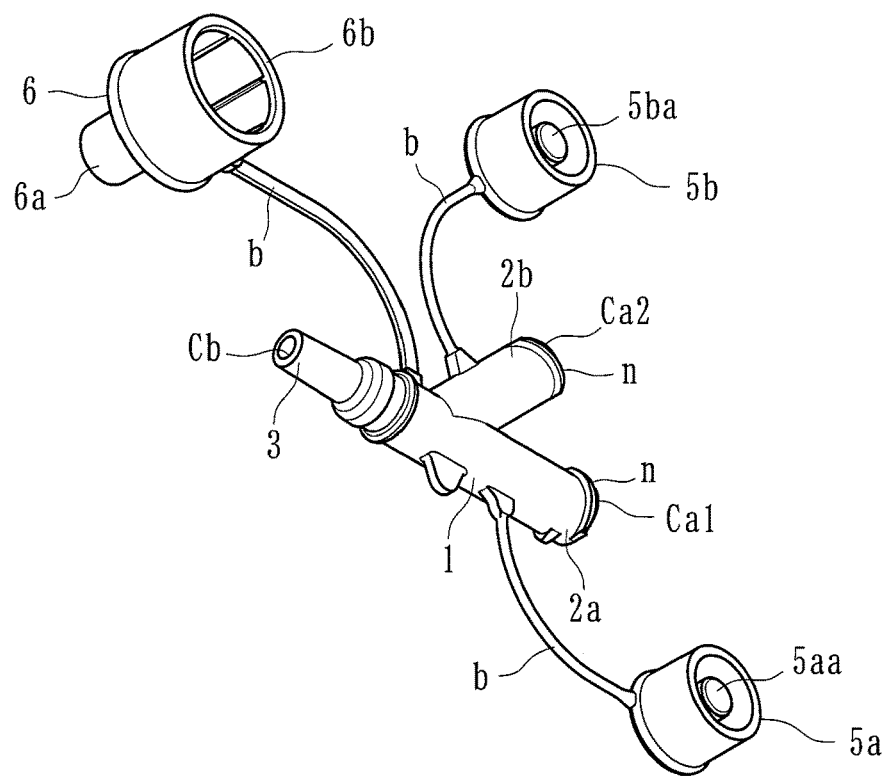

[Fig. 7]
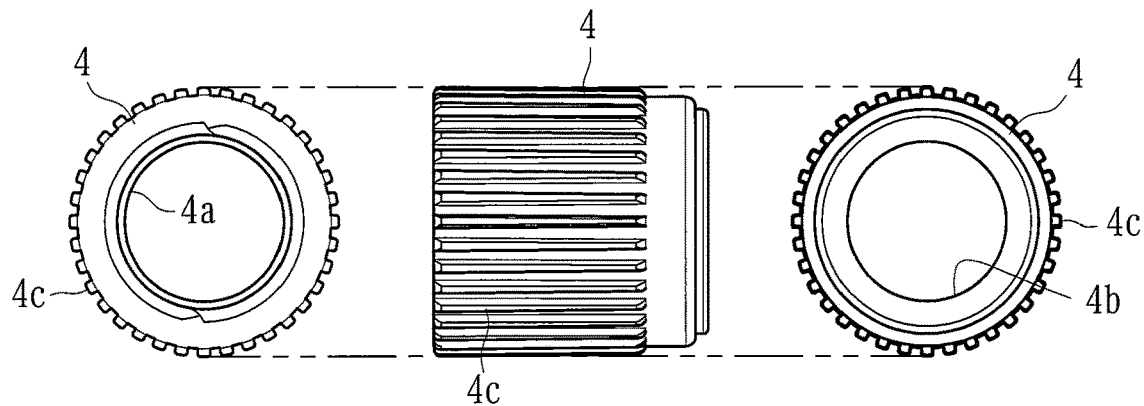
[Fig. 8]
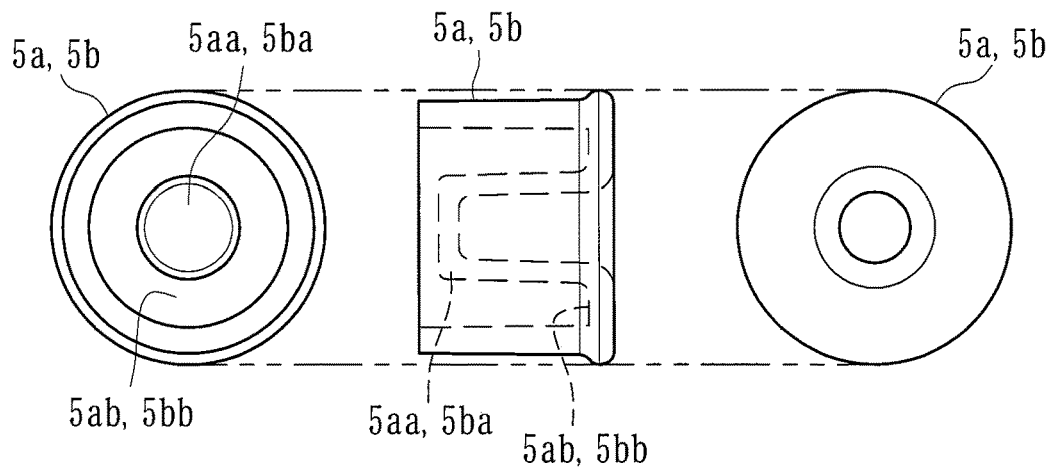
[Fig. 9]
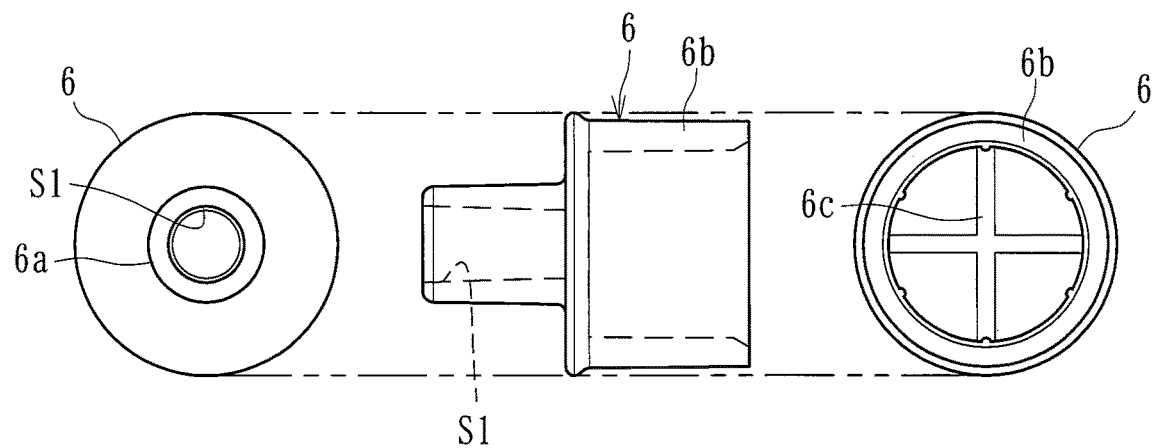

[Fig. 10]
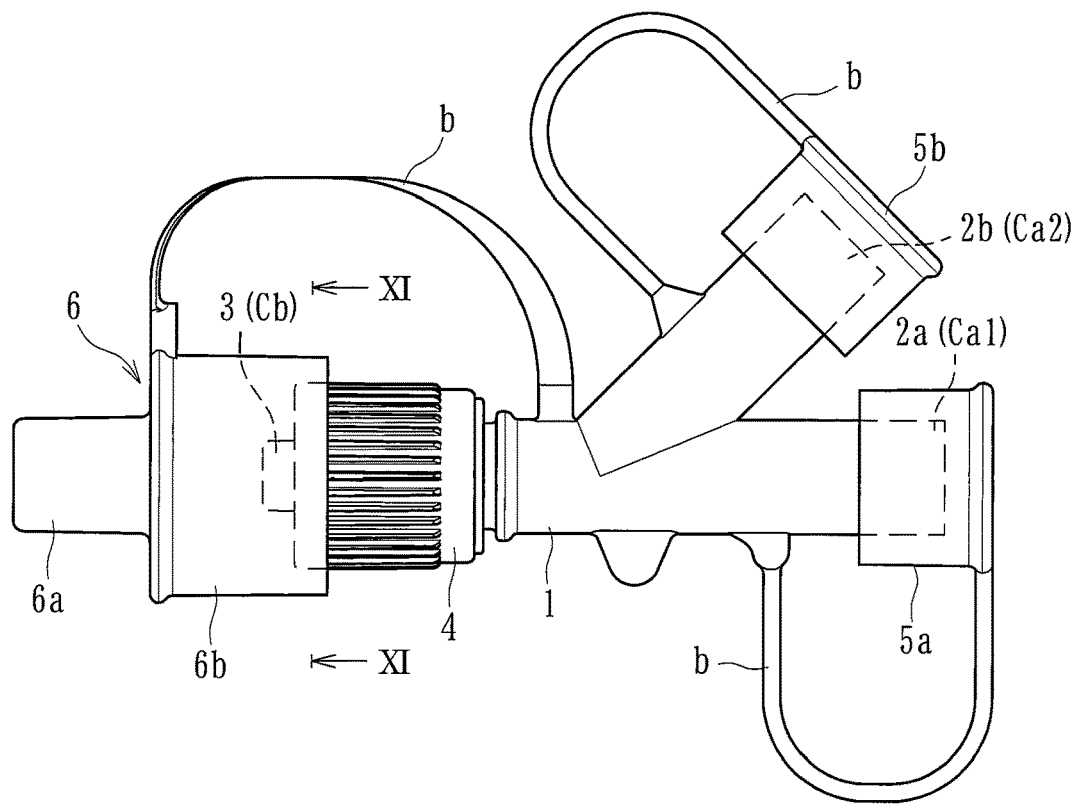
[Fig. 11]
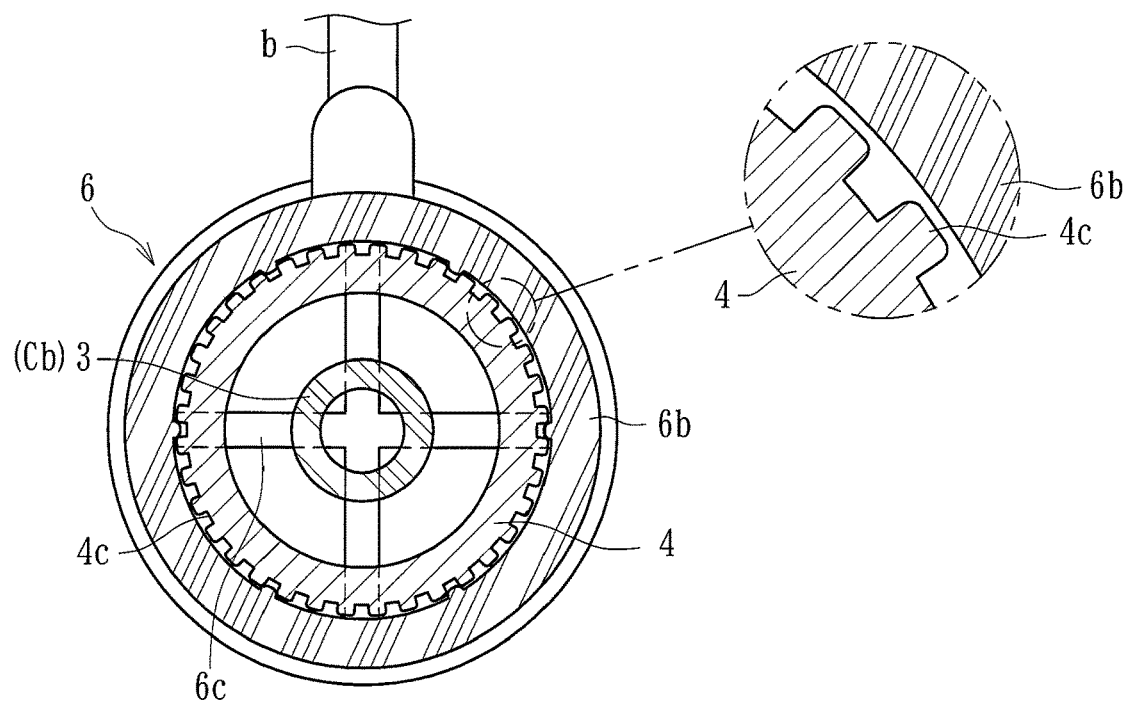

[Fig. 12]
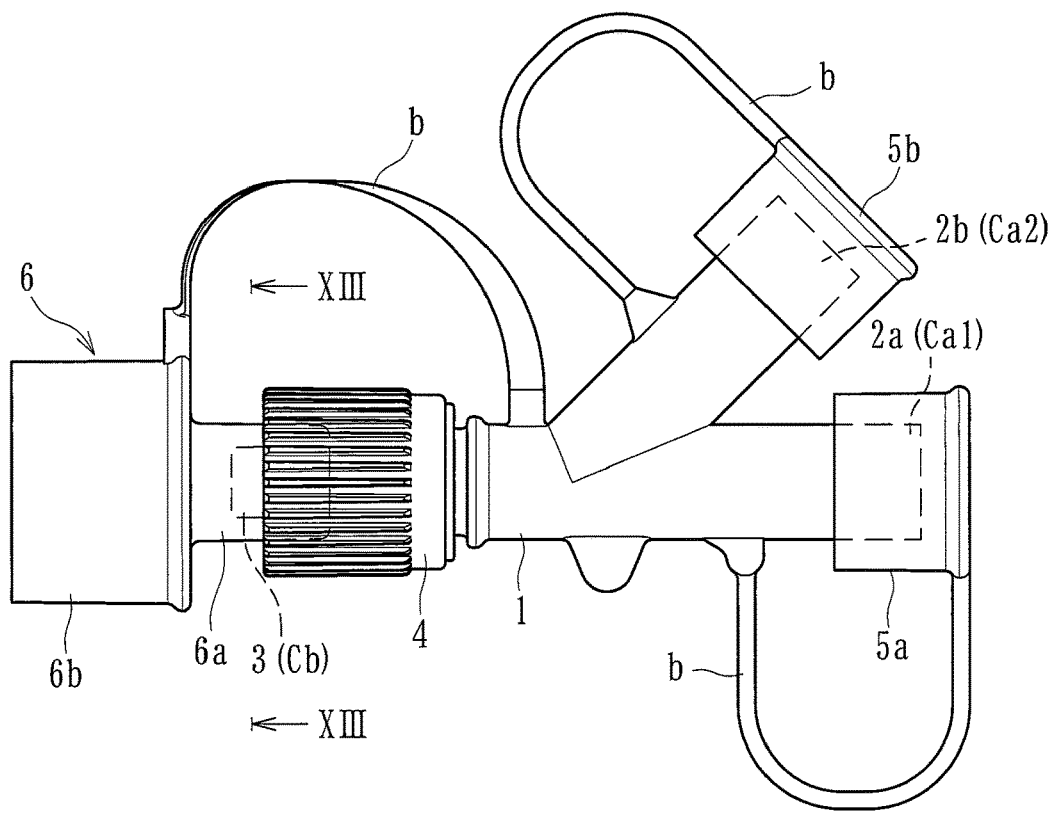
[Fig. 13]
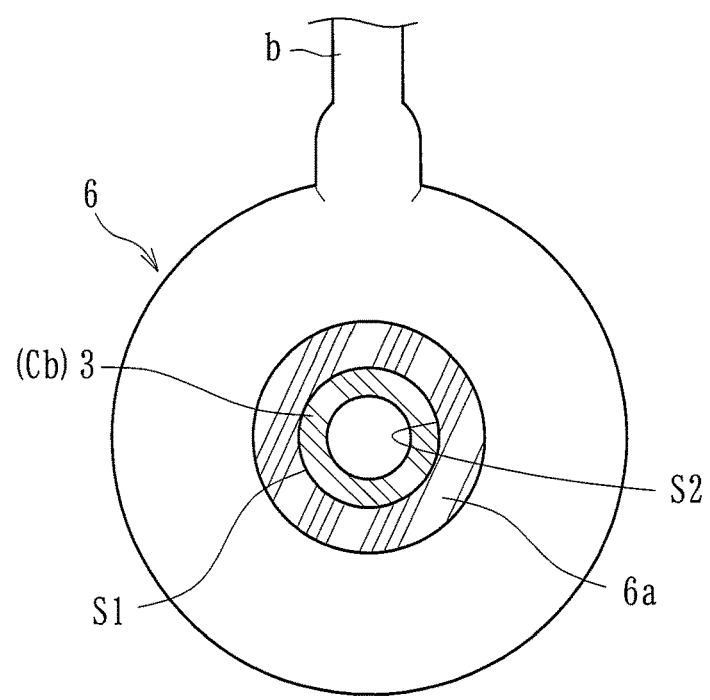

[Fig. 14]
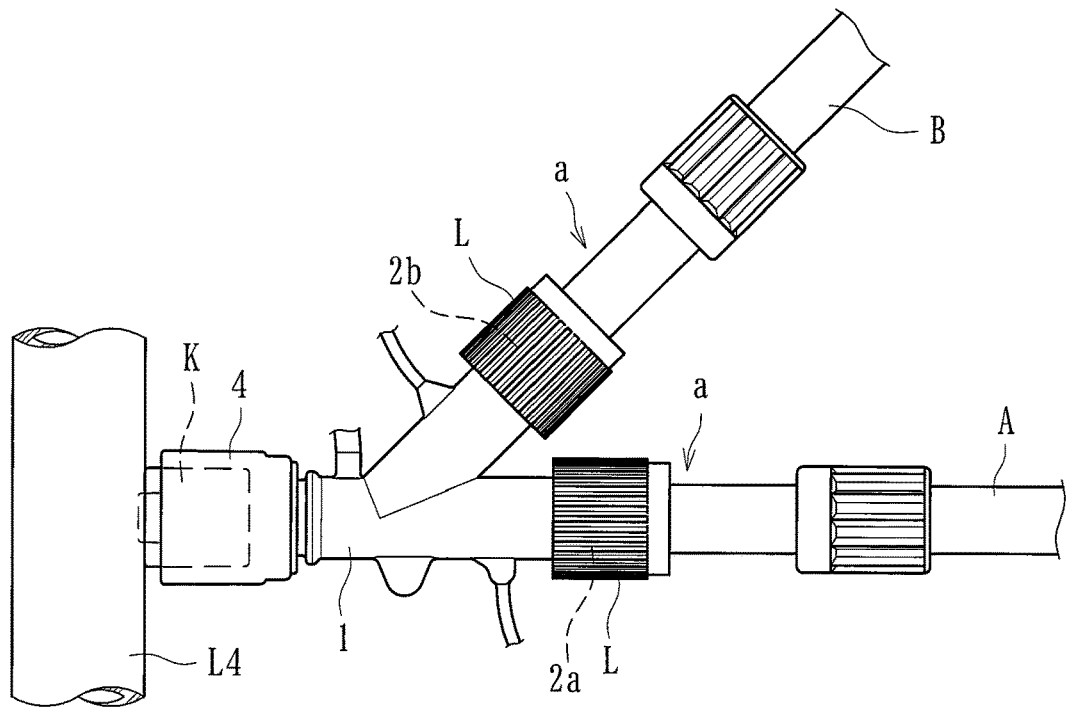
[Fig. 15]
(a)
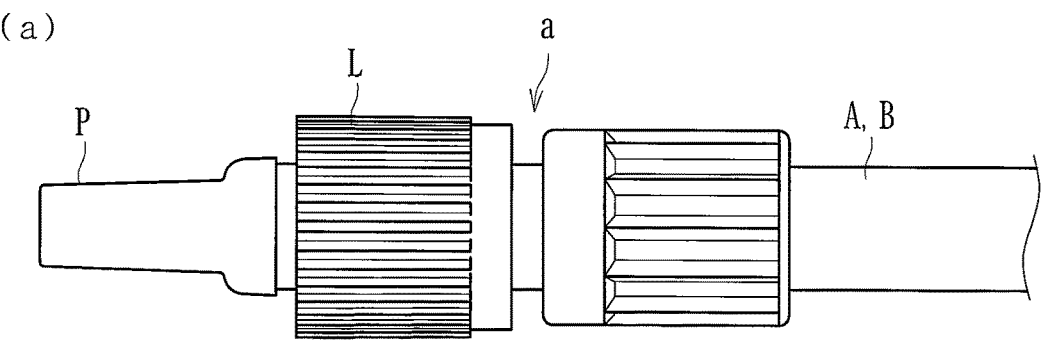
(b)
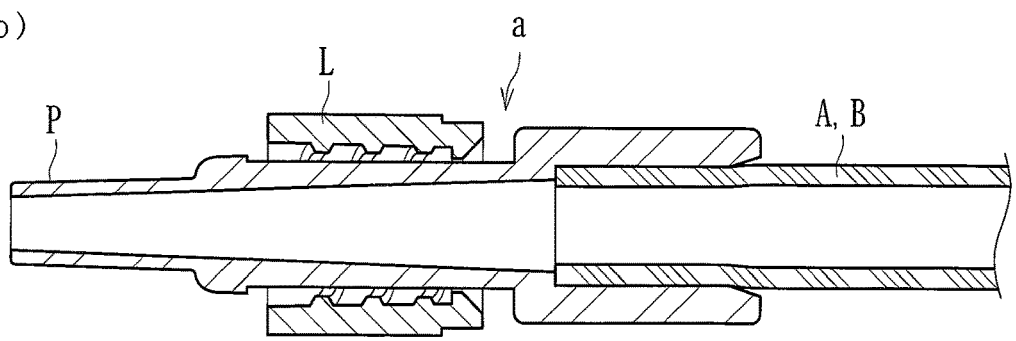

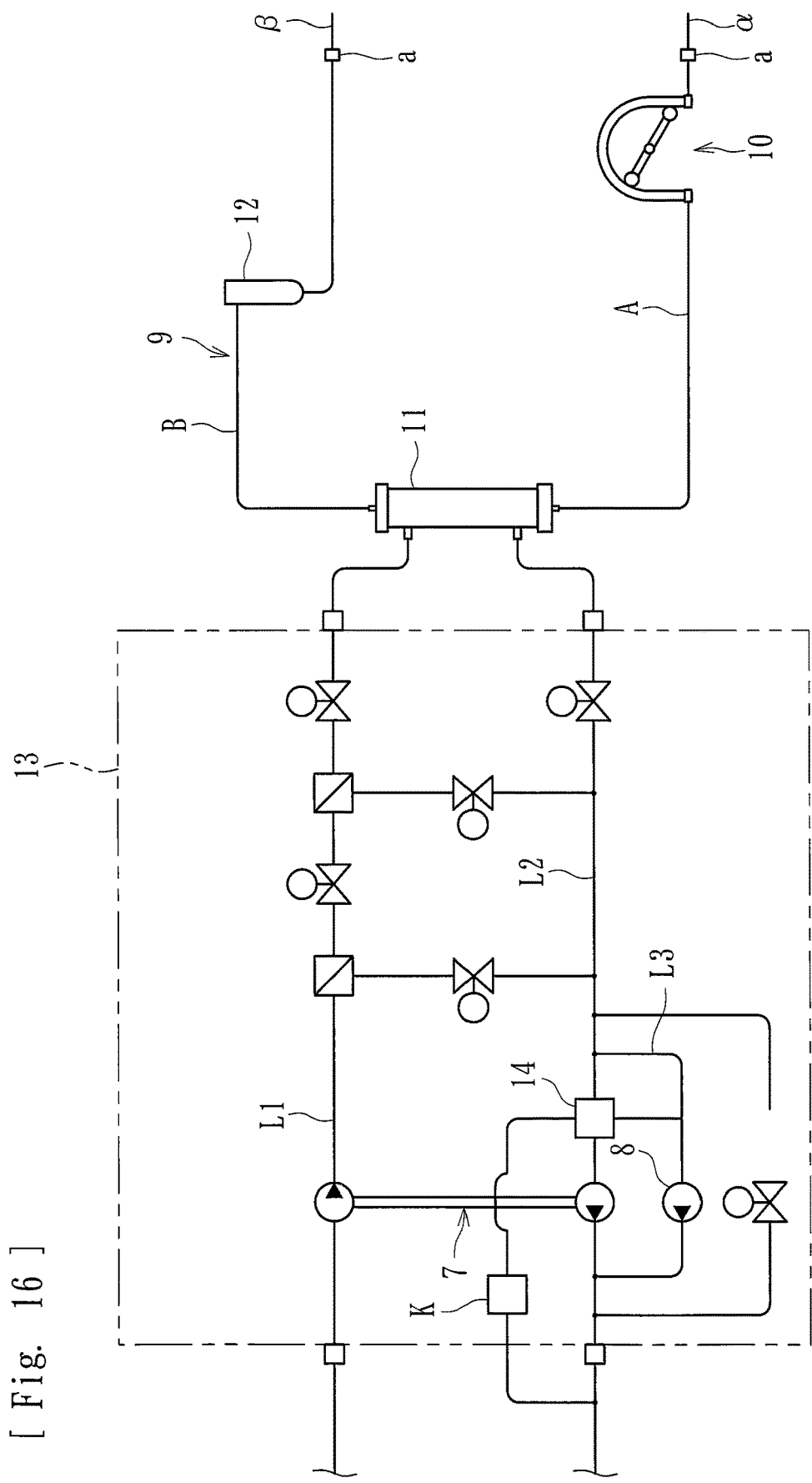
[Fig. 16]

[Fig. 17]
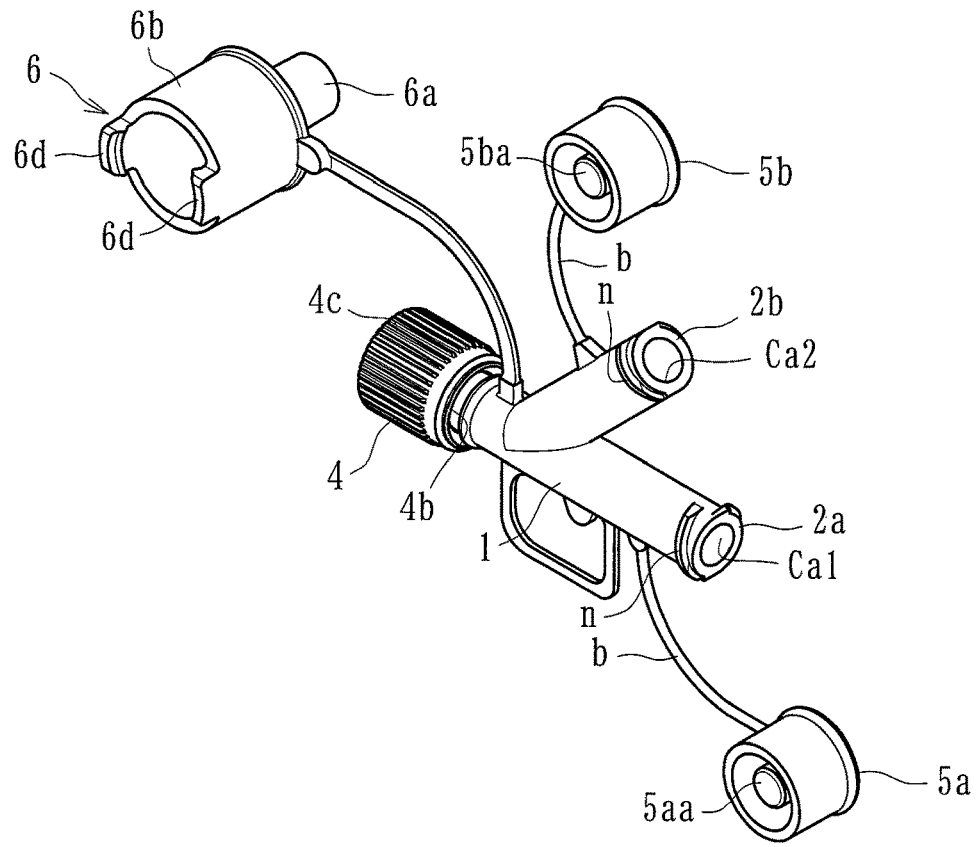
[Fig. 18]
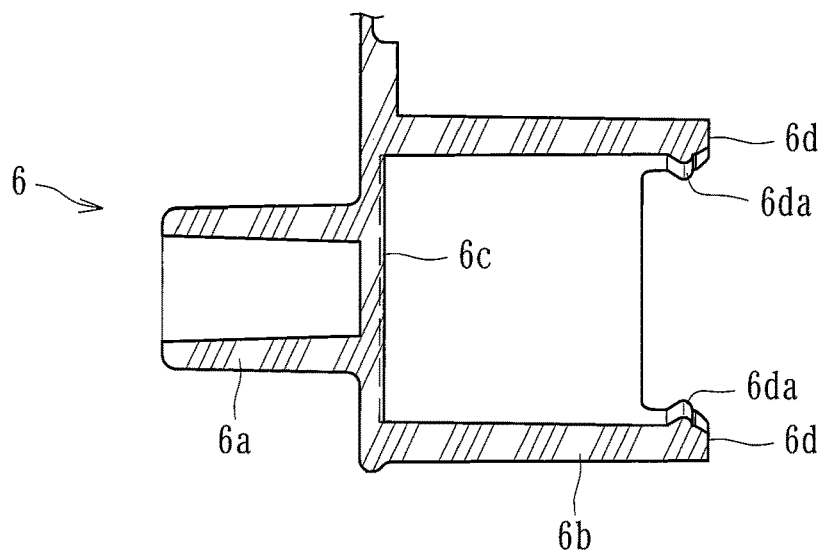

MEDICAL CONNECTOR

FIELD

The present invention relates to a medical connector to be provided between and connectable to one flow route and an other flow route through which liquid is allowed to flow.

BACKGROUND

In general, a blood circuit for causing blood of a patient to extracorporeally circulate in blood purification treatment includes an arterial blood circuit and a venous blood circuit that are formed of flexible tubes. A blood purifier (a dialyzer or the like) for purifying the blood in extracorporeal circulation is connected to a proximal end of the arterial blood circuit and to a proximal end of the venous blood circuit. Furthermore, an arterial puncture needle and a venous puncture needle to be stuck into the patient are attachable to distal ends of the respective blood circuits.

In general, such a blood circuit is subjected to a priming step for performing flushing or the like with a priming solution supplied thereinto and caused to flow therethrough before the treatment (before the blood is caused to extracorporeally circulate). The priming step is performed by using a medical connector, occasionally. A known medical connector is a Y-shaped manifold including a body having an internal flow route through which a priming solution or the like introduced thereinto from a blood circuit is allowed to flow; two one-side connection ports connectable to a distal end of an arterial blood circuit and a distal end of a venous blood circuit, respectively; and one other-side connection port connectable to a connection port of a drainage device (for example, a connection port of a dialysate drain line or the like through which waste liquid discharged from the blood purifier is discharged to the outside).

In the priming step, the distal end of the arterial blood circuit and the distal end of the venous blood circuit are connected to the respective one-side connection ports, and the other-side connection port is connected to the connection port of the drainage device. In this state, the priming solution introduced from a particular part (such as an overflow line extending from an air-trap chamber) of the blood circuit can be caused to flow through the arterial blood circuit and the venous blood circuit and to be discharged to the drainage device through the internal flow route of the medical connector.

The known medical connector has caps that prevent the worker from directly touching the connection ports with the hands. Usually, the one-side connection ports and the other-side connection port are covered by the caps, respectively, at the time of shipment. Meanwhile, the medical connector needs to be sterilized in advance by vapor sterilization or the like, as with other disposable tools such as the blood circuit. Therefore, for example, the cap for covering the other-side connection port does not seal the connection port but allows ventilation of vapor used in vapor sterilization. Such a known technique is not disclosed by any publicly known invention. Hence, there is no information on prior art to be cited.

SUMMARY

In the above known medical connector, the cap for covering the other-side connection port does not seal the connection port but allows ventilation of vapor used in vapor sterilization. Therefore, when the priming step is finished and the medical connector is disconnected for disposal from the connection ports of the blood circuit and the drainage device, the connection ports need to be sealed by using a separately provided clamping device such as a pair of forceps so that the priming solution used in the priming step and remaining in the internal flow route is prevented from leaking to the outside.

The present invention has been conceived in view of the above circumstances and provides a medical connector that allows ventilation of vapor used in vapor sterilization and has an internal flow route that is tightly closable without using any separate clamping device.

According to the teachings herein, there is provided a medical connector to be provided between and connectable to one flow route and an other flow route through which liquid is allowed to flow. The medical connector includes a body having an internal flow route through which the liquid flowing in the one flow route is allowed to flow into the other flow route, a proximal portion included in the body and having a one-side connection port at which the internal flow route is connectable to the one flow route, a distal portion included in the body and having an other-side connection port at which the internal flow route is connectable to the other flow route, a one-side lid portion with which the one-side connection port is closable, and an other-side lid portion whose state is switchable between a closing state in which the other-side lid portion closes the other-side connection port such that the internal flow route is tightly closed and a ventilating state in which the other-side lid portion covers the other-side connection port such that ventilation is allowed.

According to the teachings herein, in the medical connector taught herein, a locking portion with which the other-side connection port connected to the other flow route is lockable is provided on an outer periphery of the other-side connection port; and the other-side lid portion in the closing state is tightly in contact with an inner peripheral surface or an outer peripheral surface of the other-side connection port such that the other-side connection port is sealed, and the other-side lid portion in the ventilating state is in contact with the locking portion and covers the other-side connection port such that ventilation is allowed.

According to the teachings herein, in the medical connector taught herein, the other-side lid portion includes a closing part that establishes the closing state and a covering part that establishes the ventilating state; and the covering part has a rib integrally formed on the covering part and with which ventilation through the other-side connection port is allowed.

According to the teachings herein, in the medical connector taught herein, the other-side lid portion is a cap-like member including the closing part at one end face and the covering part at an other end face.

According to the teachings herein, in the medical connector taught herein, the medical connector is a manifold including a plurality of proximal portions each being the proximal portion; and the one-side connection port provided in the respective proximal portions are closable with respective one-side lid portions each being the one-side lid portion.

According to the teachings herein, in the medical connector taught herein, the one flow route includes an arterial blood circuit and a venous blood circuit for causing blood of a patient to extracorporeally circulate; the one-side connection ports include a first one-side connection port connectable to a distal portion of the arterial blood circuit and a second one-side connection port connectable to a distal portion of the venous blood circuit; and liquid that is caused to flow through the arterial blood circuit and the venous blood circuit is dischargeable from the other-side connection port.

According to the teachings herein, there is provided a blood circuit in which the arterial blood circuit or the venous blood circuit is connected to the one-side connection port of the medical connector taught herein.

According to the teachings herein, the medical connector includes the other-side lid portion whose state is switchable between the closing state in which the other-side lid portion closes the other-side connection port such that the internal flow route is tightly closed and the ventilating state in which the other-side lid portion covers the other-side connection port such that ventilation is allowed. Therefore, while ventilation of vapor used in vapor sterilization is allowed, the internal flow route can be tightly closed without using any separate clamping device.

According to the teachings herein, the locking portion with which the other-side connection port connected to the other flow route is lockable is provided on the outer periphery of the other-side connection port. Furthermore, the other-side lid portion in the closing state is tightly in contact with the inner peripheral surface or the outer peripheral surface of the other-side connection port such that the other-side connection port is sealed, whereas the other-side lid portion in the ventilating state is in contact with the locking portion and covers the other-side connection port such that ventilation is allowed. Therefore, while sealing in the closing state can be realized assuredly, ventilation of vapor in the ventilating state can be realized in good manner.

According to the teachings herein, the other-side lid portion includes the closing part that establishes the closing state, and the covering part that establishes the ventilating state. The covering part has the rib integrally formed thereon and with which ventilation through the other-side connection port is allowed. Therefore, ventilation of vapor in the ventilating state can be realized in good manner with a simple configuration.

According to the teachings herein, the other-side lid portion is a cap-like member including the closing part at one end face and the covering part at the other end face. Therefore, the switching between the closing state and the ventilating state can be realized by turning over the cap-like member.

According to the teachings herein, the medical connector is a manifold including a plurality of proximal portions. Furthermore, the one-side connection ports provided in the respective proximal portions are closable with the respective one-side lid portions. Therefore, vapor sterilization of the manifold can be performed assuredly, and the internal flow route can be tightly closed assuredly.

According to the teachings herein, the one-side connection ports include the first one-side connection port that is connectable to the distal portion of the arterial blood circuit, and the second one-side connection port that is connectable to the distal portion of the venous blood circuit. Furthermore, liquid that is caused to flow through the arterial blood circuit and the venous blood circuit is dischargeable from the other-side connection port. Therefore, the priming solution used in the priming of the blood circuit or any other like liquid can be drained through the other-side connection port. Furthermore, the priming solution remaining after the priming or any other like liquid can be tightly confined in the internal flow route.

According to the teachings herein, a blood circuit producing the same advantageous effects as taught herein can be provided.

BRIEF DESCRIPTION OF THE DRAWINGS

FIG. 1 is a front view of a medical connector according to an embodiment of the present invention.
FIG. 2 is a side view of the medical connector.
FIG. 3 is a perspective view of the medical connector.
FIG. 4 is a perspective view of the medical connector.
FIG. 5 is a vertical sectional view of the medial connector.
FIG. 6 is a perspective view of the medical connector (in a state before a locking portion is attached thereto).
FIG. 7 is a three-view projection illustrating the locking portion of the medical connector.
FIG. 8 is a three-view projection illustrating a one-side lid portion of the medical connector.
FIG. 9 is a three-view projection illustrating an other-side lid portion of the medical connector.
FIG. 10 is a front view of the medical connector, with the other-side lid portion being in a ventilating state.
FIG. 11 is a sectional view taken along line XI-XI illustrated in FIG. 10.
FIG. 12 is a front view of the medical connector, with the other-side lid portion being in a closing state.
FIG. 13 is a sectional view taken along line XIII-XIII illustrated in FIG. 12.
FIG. 14 is a schematic diagram illustrating the medical connector in a state where distal portions of an arterial blood circuit and a venous blood circuit are connected to one-side connection ports, respectively, while an other-side connection port is connected to a drain port of a dialysis apparatus.
FIG. 15 is a schematic diagram illustrating the distal portion of the arterial blood circuit or the venous blood circuit to be connected to the medical connector, in external view in part (a) and in sectional view in part (b).
FIG. 16 is a schematic diagram illustrating a blood circuit and a dialysis apparatus to which the medical connector is applied.
FIG. 17 is a perspective view of a medical connector according to another embodiment of the present invention.
FIG. 18 is a vertical sectional view of an other-side lid portion of the medical connector.

DETAILED DESCRIPTION

Embodiments of the present invention will now be described specifically with reference to the drawings.

A medical connector according to an embodiment is to be provided between and connectable to one flow route and an other flow route through which liquid is allowed to flow. As illustrated in FIGS. 1 to 6, the medical connector includes a body 1, two proximal portions (2a and 2b) included in the body 1, one distal portion 3 included in the body 1, a locking portion 4, two one-side lid portions (5a and 5b) connected to the body 1 with respective band parts b, and one other-side lid portion 6 connected to the body 1 with another band part b.

The body 1 is an integrally molded component made of, for example, resin and having an internal flow route R (see FIG. 5) that allows liquid flowing in the one flow route to flow into the other flow route. The body 1 is a manifold including a plurality (two in the present embodiment) of proximal portions (2a and 2b). Hence, the internal flow route R forms a substantially Y-shaped flow route in which a flow route in the proximal portion 2a and a flow route in the proximal portion 2b merge together in a middle part, and the merged flow route extends through to the distal portion 3.

The proximal portions (2a and 2b) are provided on a proximal side of the body 1 and include a first one-side connection port Ca1 and a second one-side connection port Ca2, respectively, at each of which the internal flow route R is connectable to the one flow route (such as a blood circuit). The proximal portions (2a and 2b) also include helical threaded parts n integrally formed therein near the first one-side connection port Ca1 and the second one-side connection port Ca2, respectively.

The distal portion 3 is provided on a distal side of the body 1 and includes an other-side connection port Cb at which the internal flow route R is connectable to the other flow route (such as a drain line of a dialysis apparatus). As illustrated in FIG. 6, the distal portion 3 has a diameter that becomes smaller toward the distal end, and the other-side connection port Cb forms a male connection port. The locking portion 4 is provided on the outer periphery of the distal portion 3. The other-side connection port Cb connected to the other flow route is lockable with the locking portion 4.

The locking portion 4 is a cylindrical component made of resin and provided separately from the body 1. As illustrated in FIG. 7, the locking portion 4 has a through hole 4b, into which the outer periphery of the distal portion 3 is fitted with play. The inner peripheral surface of the through hole 4b has a helical part 4a integrally formed therein. As illustrated in FIG. 14, the other-side connection port Cb in the distal portion 3 is connected to a drain port K. In this state, the helical part 4a of the locking portion 4 is made to mesh with a threaded part (not illustrated) provided in the drain port K, whereby the distal portion 3 connected to the drain port K can be locked. Furthermore, the locking portion 4 has rugged part 4c over the entirety, in the peripheral direction, of the outer peripheral surface thereof. The rugged part 4c forms serrations. Such serrations prevent fingers of the worker from slipping when the locking portion 4 is made to mesh with and locked to the object of connection.

The one-side lid portions (5a and 5b) are resin members with which the first one-side connection port Ca1 and the second one-side connection port Ca2 are closable, respectively. As illustrated in FIG. 8, the one-side lid portions (5a and 5b) are each a bottomed cylindrical member, with a projection (5aa or 5ba) projecting from a central part of a bottom (5ab or 5bb) thereof. When the one-side lid portions (5a and 5b) are attached to the proximal portions (2a and 2b) (see FIGS. 10 and 12), the projections (5aa and 5ba) are press-fitted into and close (seal) the first one-side connection port Ca1 and the second one-side connection port Ca2, respectively.

The other-side lid portion 6 is a resin member whose state is switchable between a closing state (see FIG. 12) in which the other-side lid portion 6 closes the other-side connection port Cb such that the internal flow route R is tightly closed and a ventilating state (see FIG. 10) in which the other-side lid portion 6 covers the other-side connection port Cb such that ventilation is allowed. As illustrated in FIG. 9, the other-side lid portion 6 includes a closing part 6a that establishes the closing state, and a covering part 6b that establishes the ventilating state. The covering part 6b includes a rib 6c integrally formed thereon and with which ventilation through the other-side connection port Cb is allowed.

Specifically, when the other-side lid portion 6 is in the closing state, as illustrated in FIG. 13, an inner peripheral surface S2 of the closing part 6a is tightly in contact with an outer peripheral surface S1 of the other-side connection port Cb, whereby the other-side connection port Cb is sealed. When the other-side lid portion 6 is in the ventilating state, as illustrated in FIG. 11, the rib 6c provided on the inner bottom surface of the covering part 6b is in contact with the open part of the distal portion 3, whereby the other-side connection port Cb is covered such that ventilation is allowed. Specifically, the rib 6c provided on the inner bottom surface of the covering part 6b has a crisscross shape with a width smaller than the inside diameter of the open part of the distal portion 3. Therefore, when the covering part 6b is covering the locking portion 4 (in the ventilating state), gaps are provided between the open part of the distal portion 3 and the inner bottom surface of the covering part 6b. Hence, ventilation is allowed through the gaps. Note that when the covering part 6b is covering the locking portion 4 (in the ventilating state), other gaps are also provided between the outer peripheral surface of the locking portion 4 (the surface having the rugged part 4c) and the inner peripheral surface of the covering part 6b (see the enlarged part in FIG. 11).

The other-side lid portion 6 according to the present embodiment is a cap-like member having the closing part 6a at one end face and the covering part 6b at the other end face, and the state of the other-side lid portion 6 is switchable between the closing state and the ventilating state by switching the side thereof to be attached to the distal portion 3. Note that the other-side lid portion 6 in the closing state may seal the other-side connection port Cb with the outer peripheral surface of the closing part 6a being tightly in contact with the inner peripheral surface of the other-side connection port Cb.

As illustrated in FIG. 16, the one flow route according to the present embodiment includes an arterial blood circuit A and a venous blood circuit B for causing blood of a patient to extracorporeally circulate. As illustrated in FIG. 14, the first one-side connection port Ca1 is connected to a distal portion (a connector a) of the arterial blood circuit A, and the second one-side connection port Ca2 is connected to a distal portion (a connector a) of the venous blood circuit B. As illustrated in FIG. 14, the other flow route according to the present embodiment is a tube (a waste-liquid flow route L4) included in a dialysis-apparatus body. When the other-side connection port Cb is connected to the drain port K provided to the tube (the waste-liquid flow route L4) as illustrated in FIG. 14, liquid that is caused to flow through the arterial blood circuit A and the venous blood circuit B can be discharged into the tube (the waste-liquid flow route L4) through the other-side connection port Cb.

The medical connector according to the present embodiment is subjected to a vapor sterilization step before factory shipment. In the vapor sterilization, containers and tools to be used in the treatment are exposed to hot vapor for sterilization. In the case of the medical connector, the vapor needs to be applied to the outer surfaces and to the internal flow route R. Therefore, at the time of vapor sterilization, the one-side lid portions (5a and 5b) are detached from the first one-side connection port Ca1 and the second one-side connection port Ca2, whereas the other-side lid portion 6 in the ventilating state is attached to the other-side connection port Cb. Accordingly, vapor introduced into the internal flow route R flows through the other-side connection port Cb and is discharged. Thus, vapor sterilization can be performed assuredly and in good manner. On the other hand, when the medical connector is used, the other-side connection port Cb is covered by the covering part 6b of the other-side lid portion 6 and is therefore prevented from being directly touched by the worker.

Now, a blood purification apparatus according to the present embodiment will be described.

The blood purification apparatus is a hemodialysis apparatus for giving hemodialysis treatment to a patient and basically includes, as illustrated in FIG. 16, a blood circuit 9 (including the arterial blood circuit A provided with a blood pump 10, and the venous blood circuit B provided with an air-trap chamber 12), and a dialysis-apparatus body 13 including a dialysate introduction line L1 and a dialysate drain line L2.

The arterial blood circuit A and the venous blood circuit B are provided with the connectors a at the respective distal portions. An arterial puncture needle α and a venous puncture needle β are attachable to the respective connectors a. As illustrated in FIG. 15, the connectors a are each a resin component including a connection-insertion part P and provided with a locking device L. The connection-insertion part P has a tapered surface with a diameter decreasing toward the tip. The locking device L has a helical thread in the inner peripheral surface.

A dialyzer 11 is provided for purifying blood. The dialyzer 11 is connected to the blood circuit 9 (the arterial blood circuit A and the venous blood circuit B), to the dialysate introduction line L1, and to the dialysate drain line L2. When the blood pump 10 is activated, blood of the patient collected through the arterial puncture needle α is caused to extracorporeally circulate through the arterial blood circuit A and the venous blood circuit B, is purified and ultrafiltered by the dialyzer 11, and is returned to the patient through the venous puncture needle β.

The dialysate introduction line L1 forms a flow route for introducing dialysate prepared to have a predetermined concentration into the dialyzer 11. The dialysate drain line L2 forms a flow route for draining the dialysate (waste liquid) drained from the dialyzer 11 to the outside. In the dialysis-apparatus body 13, a duplex pump 7 (a reciprocating pump) as a liquid-delivering device that delivers the dialysate prepared to have a predetermined concentration to the dialyzer 11 and causes the dialysate (waste liquid) flowing from the dialyzer 11 to be drained to the outside is connected to the dialysate introduction line L1 and to the dialysate drain line L2. The dialysis-apparatus body 13 includes a plurality of bypass lines and a plurality of electronic valves provided at respective positions. A bypass line L3 for bypassing a drain-side pump chamber of the duplex pump 7 is provided with an ultrafiltration pump 8.

The dialysate drain line L2 is provided with a degassing chamber 14 for degassing at a position on the upstream side with respect to the drain-side pump chamber of the duplex pump 7. The degassing chamber 14 is provided with the waste-liquid flow route L4 at the top. The waste-liquid flow route L4 is connected at one end thereof to the position of the dialysate drain line L2 that is on the upstream side with respect to the drain-side pump chamber of the duplex pump 7, as described above, and at the other end thereof to a position of the dialysate drain line L2 that is on the downstream side with respect to the drain-side pump chamber of the duplex pump 7. The drain port K is provided at a halfway position of the waste-liquid flow route L4.

To perform a priming step before the treatment, as illustrated in FIG. 14, the connection-insertion parts P of the connectors a at the distal portions of the arterial blood circuit A and the venous blood circuit B (in a state before the arterial puncture needle α and the venous puncture needle β are attached) are inserted into and thus connected to the first one-side connection port Ca1 and the second one-side connection port Ca2, respectively, of the medical connector according to the present embodiment. Then, the helical threads provided in the inner peripheral surfaces of the respective locking devices L are made to mesh with the threaded parts n provided in the respective proximal portions (2a and 2b), whereby the connected state is locked.

Subsequently, the other-side connection port Cb in the distal portion 3 of the medical connector is inserted into and thus connected to the drain port K provided at the specified position of the dialysis-apparatus body 13. Furthermore, the helical part 4a of the locking portion 4 is made to mesh with the threaded part (not illustrated) of the drain port K, whereby the distal portion 3 connected to the drain port K is locked. Thus, the arterial blood circuit A and the venous blood circuit B forming "the one flow route" according to the present invention can be connected to the first one-side connection port Ca1 and the second one-side connection port Ca2, respectively, provided in the proximal portions (2a and 2b) of the medical connector, and the other-side connection port Cb provided in the distal portion 3 can be connected to the waste-liquid flow route L4 forming the "other flow route" according to the present invention.

Subsequently, a priming solution is supplied into the blood circuit 9 (the arterial blood circuit A and the venous blood circuit B) through a priming-solution supply line, which is not illustrated. The thus supplied priming solution can be discharged into the waste-liquid flow route L4 through the internal flow route R of the medical connector. The waste-liquid flow route L4 is connected to the dialysate drain line L2 provided in the dialysis-apparatus body 13. Therefore, the priming solution discharged from the medical connector flows through the waste-liquid flow route L4 and into the dialysate drain line L2, and is discharged to the outside from the dialysate drain line L2.

When priming is finished as described above, the blood circuit 9 (the arterial blood circuit A and the venous blood circuit B) is disconnected from the first one-side connection port Ca1 and the second one-side connection port Ca2. Then, the first one-side connection port Ca1 and the second one-side connection port Ca2 are closed by using the one-side lid portions (5a and 5b). Furthermore, the other-side connection port Cb is disconnected from the drain port K, and the other-side connection port Cb is closed by using the closing part 6a of the other-side lid portion 6, so that the internal flow route R is tightly closed. Thus, liquid (the priming solution) remaining in the internal flow route R can be prevented from leaking to the outside. Furthermore, the used medical connector can be disposed of easily.

According to the present embodiment, the medical connector includes the other-side lid portion 6 whose state is switchable between the closing state in which the other-side lid portion 6 closes the other-side connection port Cb such that the internal flow route R is tightly closed and the ventilating state in which the other-side lid portion 6 covers the other-side connection port Cb such that ventilation is allowed. Therefore, while ventilation of vapor used in vapor sterilization is allowed, the internal flow route R can be tightly closed without using any separate clamping device. Hence, with the present medical connector, vapor sterilization before use can be performed assuredly. Furthermore, the used medical connector can be disposed of easily.

On the other hand, the locking portion 4 with which the other-side connection port Cb connected to the other flow route (in the present embodiment, the waste-liquid flow route L4) is lockable is provided on the outer periphery of the other-side connection port Cb. Furthermore, the other-side lid portion 6 in the closing state is tightly in contact with the inner peripheral surface or the outer peripheral surface of the other-side connection port Cb such that the other-side connection port Cb is sealed, whereas the other-side lid portion 6 in the ventilating state is in contact with the locking portion 4 and covers the other-side connection port Cb such that ventilation is allowed. Therefore, while sealing in the closing state can be realized assuredly, ventilation of vapor in the ventilating state can be realized in good manner.

The other-side lid portion 6 according to the present embodiment includes the closing part 6a that establishes the closing state, and the covering part 6b that establishes the ventilating state. The covering part 6b has the rib 6c integrally formed thereon and with which ventilation through the other-side connection port Cb is allowed. Therefore, ventilation of vapor in the ventilating state can be realized in good manner with a simple configuration. In particular, since the other-side lid portion 6 according to the present embodiment is a cap-like member including the closing part 6a at one end face and the covering part 6b at the other end face, the switching between the closing state and the ventilating state can be realized by turning over the cap-like member.

The medical connector according to the present embodiment is a manifold including a plurality (two in this embodiment) of proximal portions (2a and 2b). Furthermore, the one-side connection ports (the first one-side connection port Ca1 and the second one-side connection port Ca2) provided in the respective proximal portions (2a and 2b) are closable with the respective one-side lid portions (5a and 5b). Therefore, vapor sterilization of the manifold can be performed assuredly, and the internal flow route R can be tightly closed assuredly.

The one-side connection ports (Ca1 and Ca2) include the first one-side connection port Ca1 that is connectable to the distal portion of the arterial blood circuit A, and the second one-side connection port Ca2 that is connectable to the distal portion of the venous blood circuit B. Furthermore, liquid that is caused to flow through the arterial blood circuit A and the venous blood circuit B is dischargeable from the other-side connection port Cb. Therefore, the priming solution used in the priming of the blood circuit 9 or any other like liquid can be drained through the other-side connection port Cb. Furthermore, the priming solution remaining after the priming or any other like liquid can be tightly confined in the internal flow route R.

The blood circuit 9 in which the arterial blood circuit A or the venous blood circuit B is connected to the one-side connection port (Ca1 or Ca2) of the medical connector can be provided as a blood circuit in which the priming solution used in the priming of the blood circuit 9 or any other like liquid can be drained through the other-side connection port Cb, and the priming solution remaining after the priming or any other like liquid can be tightly confined in the internal flow route R.

While the present embodiment has been described above, the present invention is not limited thereto. For example, the one flow route may be a flow route other than the blood circuit 9 (the arterial blood circuit A and the venous blood circuit B), and the other flow route may be a flow route other than the waste-liquid flow route L4 provided in the dialysis-apparatus body 13. Furthermore, the liquid that is made to flow through the one flow route, the other flow route, and the internal flow route R is not limited to the priming solution and may be any other liquid that is used in the treatment or in any work associated to the treatment.

The medical connector may include a single one-side connection port in the proximal portion, and a single other-side connection port in the distal portion. Alternatively, for example, the medical connector may include three or more one-side connection ports in the proximal portion. The other-side lid portion 6 according to the above embodiment is a cap-like member having the closing part 6a at one end face and the covering part 6b at the other end face, and the state of the other-side lid portion 6 is switchable between the closing state and the ventilating state by turning over the other-side lid portion 6. Alternatively, the switching may be implemented by any way other than turning over (for example, the ventilating state may be established when the amount of pressing into the other-side connection port is small, and the closing state may be established when the amount of pressing is large).

In addition, as illustrated in FIGS. 17 and 18, the other-side lid portion 6 of the medical connector may include a retaining part 6d on the side of the covering part 6b. The retaining part 6d includes a pair of projections serving as so-called snap-fitting parts. The projections are integrally formed on the edge of the opening of the covering part 6b in such a manner as to project therefrom. The projections each have a catch 6da at the tip. In the state where the covering part 6b is covering the locking portion 4 (in the ventilating state), gaps are provided with the presence of the rib 6c between the open part of the distal portion 3 and the inner bottom surface of the covering part 6b. Hence, ventilation is allowed through the gaps. Furthermore, since the retaining part 6d engages with (snap-fitted to) the locking portion 4, the covering part 6b is prevented from coming off the locking portion 4. The retaining part 6d according to such an embodiment may be replaced with any other element that prevents the covering part 6b from coming off the locking portion 4.

The present invention is also applicable to any medical connector having a different external shape, any additional functions, or the like, as long as the medical connector includes an other-side lid portion whose state is switchable between a closing state in which the other-side lid portion closes the other-side connection port such that the internal flow route is tightly closed and a ventilating state in which the other-side lid portion covers the other-side connection port such that ventilation is allowed.

REFERENCE SIGN LIST 1 body
2a proximal portion
2b proximal portion
3 distal portion
4 locking portion
4a helical part
4b through hole
4c rugged part
5a, 5b one-side lid portion
6 other-side lid portion
6a closing part
6b covering part
6c rib
6d retaining part
6da catch
7 duplex pump
8 ultrafiltration pump
9 blood circuit
10 blood pump
11 dialyzer
12 air-trap chamber
13 dialysis-apparatus body
14 degassing chamber
Ca1 first one-side connection port
Ca2 second one-side connection port
Cb other-side connection port
R internal flow route n threaded part
b band part
K drain port
L4 waste-liquid flow route
P connection-insertion part
L locking device

The invention claimed is:

1. A medical connector to be provided between and connectable to one flow route and an other flow route through which liquid is allowed to flow, the medical connector comprising:
   a body having an internal flow route through which the liquid flowing in the one flow route is allowed to flow into the other flow route;
   a proximal portion included in the body and having a one-side connection port at which the internal flow route is connectable to the one flow route;
   a distal portion included in the body and having an other-side connection port at which the internal flow route is connectable to the other flow route;
   a plurality of lids, at least one of the plurality of lids comprising:
      a one-side lid portion with which the one-side connection port is closable; and
   at least one of the plurality of lids comprising:
      an other-side lid portion whose state is switchable between a closing state in which a first side of the other-side lid portion is in direct contact with and closes the other-side connection port such that the internal flow route is tightly closed and a ventilating state in which a second side of the other-side lid portion is in direct contact with and covers the other-side connection port such that ventilation is allowed through the second side of the other-side lid portion.

2. The medical connector according to claim 1, wherein a locking portion with which the other-side connection port connected to the other flow route is lockable is provided on an outer periphery of the other-side connection port; and wherein the other-side lid portion in the closing state is tightly in contact with an inner peripheral surface or an outer peripheral surface of the other-side connection port such that the other-side connection port is sealed, and the other-side lid portion in the ventilating state is in contact with the locking portion and covers the other-side connection port such that ventilation is allowed.

3. The medical connector according to claim 2, wherein the other-side lid portion includes a closing part on the first side that establishes the closing state and a covering part on the second side that establishes the ventilating state; and wherein the covering part has a rib integrally formed on the covering part and with which ventilation through the other-side connection port is allowed.

4. The medical connector according to claim 3, wherein the medical connector is a manifold including a plurality of proximal portions each of the plurality of proximal portions being a proximal portion of the manifold; and wherein the one-side connection port provided in the plurality of proximal portions are closable with respective one-side lid portions each being the one-side lid portion.

5. The medical connector according to claim 2, wherein the medical connector is a manifold including a plurality of proximal portions each of the plurality of proximal portions being a proximal portion of the manifold; and wherein the one-side connection port provided in the plurality of proximal portions are closable with respective one-side lid portions each being the one-side lid portion.

6. The medical connector according to claim 1, wherein the other-side lid portion includes a closing part on the first side that establishes the closing state and a covering part on the second side that establishes the ventilating state; and wherein the covering part has a rib integrally formed on the covering part and with which ventilation through the other-side connection port is allowed.

7. The medical connector according to claim 6, wherein the other-side lid portion is a cap-like member including the closing part on the first side at one end face and the covering part on the second side at an other end face.

8. The medical connector according to claim 7, wherein the medical connector is a manifold including a plurality of proximal portions each of the plurality of proximal portions being a proximal portion of the manifold; and wherein the one-side connection port provided in the plurality of proximal portions are closable with respective one-side lid portions each being the one-side lid portion.

9. The medical connector according to claim 6, wherein the medical connector is a manifold including a plurality of proximal portions each of the plurality of proximal portions being a proximal portion of the manifold; and wherein the one-side connection port provided in the plurality of proximal portions are closable with respective one-side lid portions each being the one-side lid portion.

10. The medical connector according to claim 6, wherein the rib is located on an inner bottom surface of the covering part and is in contact with an open part of the distal portion.

11. The medical connector according to claim 1, wherein the medical connector is a manifold including a plurality of proximal portions each of the plurality of proximal portions being a proximal portion of the manifold; and wherein the one-side connection port provided in the plurality of proximal portions are closable with respective one-side lid portions each being the one-side lid portion.

12. The medical connector according to claim 11, wherein the one flow route includes an arterial blood circuit and a venous blood circuit for causing blood of a patient to extracorporeally circulate; wherein the one-side connection ports include a first one-side connection port connectable to a distal portion of the arterial blood circuit and a second one-side connection port connectable to a distal portion of the venous blood circuit; and wherein the liquid that is caused to flow through the arterial blood circuit and the venous blood circuit is dischargeable from the other-side connection port.

13. A blood circuit in which the arterial blood circuit or the venous blood circuit is connected to the one-side connection port of the medical connector according to claim 12.

14. The medical connector according to claim 1, further comprising:
   a locking portion with which the other-side connection port connected to the other flow route is lockable is provided on an outer periphery of the other-side connected port, and the other-side lid portion includes a covering part that establishes the ventilating state, wherein the locking portion includes either or both a rugged part in the locking portion or a retaining part in the covering part, and the covering part has a rib integrally formed thereon and with which ventilation through the other-side connection port is allowed.

15. The medical connector according to claim 1, wherein the state of the other-side lid portion is switchable between the closing state and the ventilating state by turning over the other-side lid portion and attaching it to the distal portion.

16. The medical connector according to claim 1, wherein a closing part has an inner peripheral surface that is tightly in contact with and seals an outer peripheral surface of the outer side connection port.

17. The medical connector according to claim 1, wherein the one side-lid portion and other-side lid portion are connected to the body with a band part.

* * * * *